(12) United States Patent
Everson et al.

(10) Patent No.: US 7,842,832 B2
(45) Date of Patent: *Nov. 30, 2010

(54) β-AMINO-α-CYANOACRYLATES AND THEIR USE AS HERBICIDES

(75) Inventors: Albert C. Everson, Cary, NC (US); Daniel J. Coughlin, Flemington, NJ (US); Michael A. Guaciaro, Clifton Park, NY (US); Linda B. Fleming, Wynatskill, NY (US); Lester L. Maravetz, Westfield, NJ (US); John L. Huppatz, Weetangera (AU)

(73) Assignee: BASF SE, Ludwigshafen (DE)

( * ) Notice: Subject to any disclaimer, the term of this patent is extended or adjusted under 35 U.S.C. 154(b) by 1316 days.

This patent is subject to a terminal disclaimer.

(21) Appl. No.: 10/499,568

(22) PCT Filed: Dec. 17, 2002

(86) PCT No.: PCT/EP02/14355

§ 371 (c)(1), (2), (4) Date: Jun. 21, 2004

(87) PCT Pub. No.: WO03/051823

PCT Pub. Date: Jun. 26, 2003

(65) Prior Publication Data

US 2005/0054536 A1    Mar. 10, 2005

(51) Int. Cl.
C07C 255/07    (2006.01)
A01N 37/34    (2006.01)

(52) U.S. Cl. ..................... 558/443; 504/312
(58) Field of Classification Search ................ 558/443; 504/312

See application file for complete search history.

(56) References Cited

U.S. PATENT DOCUMENTS 4,902,334 A * 2/1990 Azuma et al. ............. 504/176
5,198,014 A * 3/1993 Maravetz ................... 504/225

FOREIGN PATENT DOCUMENTS

EP    0 104 432    4/1984
JP    59/051202    3/1984
JP    60/078902    5/1985

OTHER PUBLICATIONS

Hayashi, et al. (AN 1968:82967 ZCAPLUS, abstract of Bulletin of Chemical SOciety of Japan (1967), 40(9), 2160-3).*
GLickman et al. (AN 1945:20676, ZCAPLUS, abstract of J. of Am. Chem Soc. (1945), 67, 1012-16).*
Campbell et al. (AN 1911:8811, ZCAPLUS, abstract of Proc. Chem. Soc. (1911), 26, 2296).*
Campbell et al. (AN 1911:8812, ZCAPLUS, abstract of J. of the Chem. Soc. Transcation (1910), 97, 2418-25).*
Baba et al. (Bull. Chem. Soc. Japan, 42 (1969) 1653-59).*
Hiramatsu et al., "Herbicide" English Abstract of document.
Hiramatsu et al., "Herbicide, Weed Killing Method and Plant-Growth Regulator" English Abstract of document.
McFadden et al,. "X-Ray Structure Analysis of a Cyanoacrylate Inhibitor of Photosystem II Electron Transport" Zeitschrift für Naturforschung C, Journal of Biosciences 46(1-2), 93-98 (1991).

* cited by examiner

Primary Examiner—Robert Havlin
(74) Attorney, Agent, or Firm—Novak Druce + Quigg LLP

(57) ABSTRACT

β-Amino-α-Cyanoacrylates of formula I where the variables have the following meanings: $R^1$ is n-alkyl, n-alkenyl or alkoxyalkyl; $R^2, R^3$ are alkyl, which may be partially or fully halogenated and/or may carry a substituent from the group consisting of cyano, alkoxy, haloalkoxy, alkylthio, haloalkylthio, $C^1$-$C^6$-alkylsulfinyl, haloalkylsulfinyl, alkylsulfonyl and haloalkylsulfonyl, are alkenyl or alkynyl; or $R^2$ and $R^3$ together with the carbon atom to which they are attached form a cycloalkyl ring in which one or two nonadjacent $CH^2$ groups may be replaced by oxygen or sulfur, and where the cycloalkyl ring may be substituted by halogen or alkyl; $R^4$ is hydrogen, halogen, cyano or alkyl, where the substituents $R^2$, $R^3$ and $R^4$ or two of the radicals $R^2$, $R^3$ and $R^4$ are not simultaneously methyl, and their agriculturally useful salts, processes and intermediates for their preparation; and the use of these compounds or of compositions comprising these compounds for controlling undesirable plants are described.

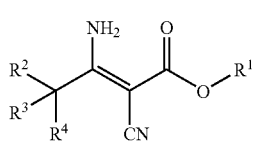

(I)

15 Claims, No Drawings

β-AMINO-α-CYANOACRYLATES AND THEIR USE AS HERBICIDES

The present invention relates to β-amino-α-cyanoacrylates of formula I

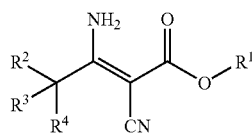

where the variables have the following meanings:
- $R^1$ is n-$C_1$-$C_6$-alkyl, n-$C_3$-$C_6$-alkenyl or $C_1$-$C_6$-alkoxy-$C_1$-$C_4$-alkyl;
- $R^2, R^3$ are $C_1$-$C_6$-alkyl, which may be partially or fully halogenated and/or may carry a substituent from the group consisting of cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl and $C_1$-$C_6$-haloalkylsulfonyl, are $C_2$-$C_6$-alkenyl or $C_2$-$C_6$-alkynyl;
  - or $R^2$ and $R^3$ together with the carbon atom to which they are attached form a $C_3$-$C_6$-cycloalkyl ring in which one or two nonadjacent $CH_2$ groups may be replaced by oxygen or sulfur, and where the $C_3$-$C_6$-cycloalkyl ring may be substituted by halogen or $C_1$-$C_4$-alkyl;
- $R^4$ is hydrogen, halogen, cyano or $C_1$-$C_6$-alkyl,
- where, if $R^1$ is n-$C_1$-$C_6$-alkyl, the substituents $R^2$, $R^3$ and $R^4$ or two of the radicals $R^2$, $R^3$ and $R^4$ are not simultaneously methyl, and their agriculturally useful salts.

Moreover, the invention relates to processes and intermediates for preparing compounds of formula I, to compositions comprising them and to the use of these derivatives or the compositions comprising them for controlling harmful plants.

α-cyano-β-aminoalkylacrylic esters are known from the literature, for example from Hayashi et al., Bull. Chem. Soc. Jpn. 40, (1967), 2160-2163. JP 61109752 discloses α,β-unsaturated carboxylic acid derivatives as plant growth regulators. WO 98/00598 (=U.S. Pat. No. 4,902,334) discloses herbicidally active crotonic acid derivatives.

However, the herbicidal properties of the prior-art compounds and/or their compatibility with crop plants are not entirely satisfactory.

It is therefore an object of the present invention to provide novel, in particular herbicidally active, compounds having improved properties.

We have found that this object is achieved by the β-amino-α-cyanoacrylates of formula I and their herbicidal activity.

Furthermore, we have found herbicidal compositions which comprise the compounds I and have very good herbicidal activity. Moreover, we have found processes for preparing these compositions and methods for controlling undesirable vegetation using compounds I.

The β-amino-α-cyanoacrylates of formula I are always present as (Z) isomers, i.e. amino group and ester radical are on the same side of the double bond.

Depending on the substitution pattern, the compounds of formula I can contain one or more chiral centers, in which case they are present as enantiomers or mixtures of diastereomers. This invention provides both the pure enantiomers or diastereomers and mixtures thereof.

The compounds of formula I can also be present in the form of their agriculturally useful salts, where the type of salt is usually immaterial. In general, suitable salts are the salts of those cations or the acid addition salts of those acids whose cations and anions, respectively, do not adversely affect the herbicidal activity of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where here, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di-(2-hydroxyeth-1-yl)ammonium, trimethylbenzylammonium, furthermore phosphonium ions, sulfonium ions, preferably tri($C_1$-$C_4$-alkyl)sulfonium, and sulfoxonium ions, preferably tri ($C_1$-$C_4$-alkyl) sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate, and also the anions of $C_1$-$C_4$-alkanoic acids, preferably formate, acetate, propionate and butyrate.

The organic moieties mentioned for the substituents $R^1$-$R^4$ are collective terms for individual enumerations of the individual group members. All hydrocarbon chains, i.e. all alkyl, alkenyl, alkynyl, haloalkyl, cyanoalkyl, alkoxy, haloalkoxy, alkylthio, haloalkylthio, alkylsulfinyl, haloalkylsulfinyl, alkylsulfonyl and haloalkylsulfonyl moieties can be straight-chain or branched. Unless indicated otherwise, halogenated substituents preferably carry one to five identical or different halogen atoms. The term halogen represents in each case fluorine, chlorine, bromine or iodine.

Examples of other meanings are:
- $C_1$-$C_4$-alkyl for example methyl, ethyl, propyl, 1-methylethyl, butyl, 1-methylpropyl, 2-methylpropyl and 1,1-dimethylethyl;
- $C_1$-$C_6$-alkyl: $C_1$-$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;
- n-$C_1$-$C_4$-alkyl: a straight-chain saturated hydrocarbon having 1 to 4 carbon atoms, such as methyl, ethyl, n-propyl and n-butyl;
- n-$C_1$-$C_6$-alkyl: n-$C_1$-$C_4$-alkyl as mentioned above, and also n-pentyl and n-hexyl;
- $C_3$-$C_6$-cycloalkyl: a monocyclic saturated hydrocarbon having 3 to 6 ring members, such as cyclopropyl, cyclobutyl, cyclopentyl and cyclohexyl;
- $C_3$-$C_6$-cycloalkyl wherein one or two non-adjacent $CH_2$ groups are replaced by oxygen or sulfur, are for example, oxiranyl, tetrahydrofuranyl, tetrahydropyranyl, thiiranyl, thietanyl, thiacyclopentyl or thiacyclohexyl;
- $C_2$-$C_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkynyl: for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl. 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_1$-$C_6$-alkoxy: for example methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_6$-alkoxy-$C_1$-$C_4$-alkyl: $C_1$-$C_4$-alkyl which is substituted by $C_1$-$C_6$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy) ethyl, 2-(1,1-dimethylethoxy) ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy) propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(butoxy)butyl, 4-(propoxy)butyl, 4-(1-methylethoxy)butyl, 4-(2-methylpropoxy)butyl and 4-(1,1-dimethylethoxy)butyl;

$C_1$-$C_6$-haloalkoxy: a $C_1$-$C_6$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_6$-alkylthio: for example methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-haloalkylthio: a $C_1$-$C_6$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio, nonafluorobutylthio, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio and dodecafluorohexylthio;

$C_1$-$C_6$-alkylsulfinyl ($C_1$-$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-Dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-haloalkylsulfinyl: a $C_1$-$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and dodecafluorohexylsulfinyl;

$C_1$-$C_6$-alkylsulfonyl ($C_1$-$C_6$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$-$C_6$-haloalkylsulfonyl: a $C_1$-$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulformyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl.

In a particular embodiment, the variables of the compounds of formula I have the following meanings, which meanings are, both on their own and in combination with one another, particular embodiments of the compounds of formula I:

Preference is given to the β-amino-α-cyanoacrylates of the formula I wherein $R^1$ is n-$C_1$-$C_6$-alkyl;
    particularly preferably n-$C_1$-$C_4$-alkyl;
    with particular preference methyl, ethyl or n-propyl.

Preference is also given to the β-amino-α-cyanoacrylates of formula I wherein $R^1$ is n-$C_3$-$C_6$-alkenyl;
    particularly preferably n-$C_3$-$C_4$-alkenyl;
    with particular preference 2-propenyl.

Preference is also given to the β-amino-α-cyanoacrylates of formula I wherein $R^2$, $R^3$ are $C_3$-$C_6$-alkyl, which may be partially or fully halogenated and/or carry a substituent from the group $C_1$-$C_6$-alkoxy;
    particularly preferably $C_1$-$C_4$-alkyl;
    with particular preference methyl or ethyl.

Preference is furthermore given to the β-amino-α-cyanoacrylates of formula I wherein $R^4$ is hydrogen, fluorine, chlorine or $C_1$-$C_4$-alkyl;
    particularly preferably hydrogen, fluorine or chlorine;
    with particular preference hydrogen.

Particular preference is given to the β-amino-α-cyanoacrylates of formula I wherein $R^1$ is n-$C_1$-$C_4$-alkyl;
    particularly preferably methyl, ethyl or n-propyl;
$R^2$, $R^3$ are $C_1$-$C_4$-alkyl;
    particularly preferably methyl or ethyl; and
$R^4$ is hydrogen, fluorine or chlorine;
    particularly preferably hydrogen.

Extraordinary preference is given to the compounds of formula I.1 (corresponds to formula I where $R^1$=CH$_3$ and $R^4$=H), in particular to the compounds of formulae I.1.1 to I.1.74 of Table 1, where the definitions of the variables $R^1$ to $R^4$ are of particular importance for the compounds according to the invention not only in combination with one another, but in each case also on their own.

TABLE 1

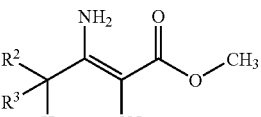

I.1

| No. | $R^2$ | $R^3$ |
|---|---|---|
| I.1.1 | $CH_3$ | $C_2H_5$ |
| I.1.2 | $CH_3$ | $nC_3H_7$ |
| I.1.3 | $CH_3$ | $iC_3H_7$ |
| I.1.4 | $CH_3$ | $nC_4H_9$ |
| I.1.5 | $CH_3$ | $CH_2CH(CH_3)_2$ |
| I.1.6 | $CH_3$ | $CH(CH_3)C_2H_5$ |
| I.1.7 | $CH_3$ | $tC_4H_9$ |
| I.1.8 | $C_2H_5$ | $C_2H_5$ |
| I.1.9 | $C_2H_5$ | $nC_3H_7$ |
| I.1.10 | $C_2H_5$ | $iC_3H_7$ |
| I.1.11 | $C_2H_5$ | $nC_4H_9$ |
| I.1.12 | $C_2H_5$ | $CH_2CH(CH_3)_2$ |
| I.1.13 | $C_2H_5$ | $CH(CH_3)C_2H_5$ |
| I.1.14 | $C_2H_5$ | $tC_4H_9$ |
| I.1.15 | $nC_3H_7$ | $nC_3H_7$ |
| I.1.16 | $nC_3H_7$ | $iC_3H_7$ |
| I.1.17 | $iC_3H_7$ | $iC_3H_7$ |
| I.1.18 | $CH_2F$ | $CH_3$ |
| I.1.19 | $CH_2F$ | $C_2H_5$ |
| I.1.20 | $CH_2F$ | $CH_2F$ |
| I.1.21 | $CH_2Cl$ | $CH_3$ |
| I.1.22 | $CH_2Cl$ | $C_2H_5$ |
| I.1.23 | $CH_2Cl$ | $CH_2Cl$ |
| I.1.24 | $CH_2Br$ | $CH_3$ |
| I.1.25 | $CH_2Br$ | $C_2H_5$ |
| I.1.26 | $CH_2Br$ | $CH_2Br$ |
| I.1.27 | $CHF_2$ | $CH_3$ |
| I.1.28 | $CHF_2$ | $C_2H_5$ |
| I.1.29 | $CHF_2$ | $CHF_2$ |
| I.1.30 | $CF_3$ | $CH_3$ |
| I.1.31 | $CF_3$ | $C_2H_5$ |
| I.1.32 | $CF_3$ | $CF_3$ |
| I.1.33 | $(CH_2)_2F$ | $CH_3$ |
| I.1.34 | $(CH_2)_2F$ | $C_2H_5$ |
| I.1.35 | $(CH_2)_2F$ | $(CH_2)_2F$ |
| I.1.36 | $(CH_2)_2Cl$ | $CH_3$ |
| I.1.37 | $(CH_2)_2Cl$ | $C_2H_5$ |
| I.1.38 | $(CH_2)_2Cl$ | $(CH_2)_2Cl$ |
| I.1.39 | $(CH_2)_2Br$ | $CH_3$ |
| I.1.40 | $(CH_2)_2Br$ | $C_2H_5$ |
| I.1.41 | $(CH_2)_2Br$ | $(CH_2)_2Br$ |
| I.1.42 | $CH_2CF_3$ | $CH_3$ |
| I.1.43 | $CH_2CF_3$ | $C_2H_5$ |
| I.1.44 | $CH_2CF_3$ | $CH_2CF_3$ |
| I.1.45 | $CH_2OCH_3$ | $CH_3$ |
| I.1.46 | $CH_2OCH_3$ | $C_2H_5$ |
| I.1.47 | $CH_2OCH_3$ | $CH_2OCH_3$ |
| I.1.48 | $(CH_2)_2OCH_3$ | $CH_3$ |
| I.1.49 | $(CH_2)_2OCH_3$ | $C_2H_5$ |
| I.1.50 | $(CH_2)_2OCH_3$ | $(CH_2)_2OCH_3$ |
| I.1.51 | $(CH_2)_3OCH_3$ | $CH_3$ |
| I.1.52 | $(CH_2)_3OCH_3$ | $C_2H_5$ |
| I.1.53 | $(CH_2)_3OCH_3$ | $(CH_2)_3OCH_3$ |
| I.1.54 | $CH(CH_3)CH_2OCH_3$ | $CH_3$ |
| I.1.55 | $CH(CH_3)CH_2OCH_3$ | $C_2H_5$ |
| I.1.56 | $CH(CH_3)CH_2OCH_3$ | $CH(CH_3)CH_2OCH_3$ |
| I.1.57 | $CH_2CH(CH_3)OCH_3$ | $CH_3$ |
| I.1.58 | $CH_2CH(CH_3)OCH_3$ | $C_2H_5$ |
| I.1.59 | $CH_2CH(CH_3)OCH_3$ | $CH_2CH(CH_3)OCH_3$ |
| I.1.60 | $CH_2OC_2H_5$ | $CH_3$ |
| I.1.61 | $CH_2OC_2H_5$ | $C_2H_5$ |
| I.1.62 | $CH_2OC_2H_5$ | $CH_2OC_2H_5$ |
| I.1.63 | $(CH_2)_2OC_2H_5$ | $CH_3$ |
| I.1.64 | $(CH_2)_2OC_2H_5$ | $C_2H_5$ |
| I.1.65 | $(CH_2)_2OC_2H_5$ | $(CH_2)_2OC_2H_5$ |
| I.1.66 | $(CH_2)_3OC_2H_5$ | $CH_3$ |
| I.1.67 | $(CH_2)_3OC_2H_5$ | $C_2H_5$ |
| I.1.68 | $(CH_2)_3OC_2H_5$ | $(CH_2)_3OC_2H_5$ |

TABLE 1-continued

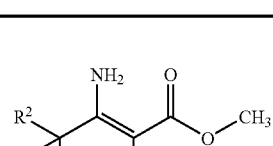

I.1

| No. | $R^2$ | $R^3$ |
|---|---|---|
| I.1.69 | $CH(CH_3)CH_2OC_2H_5$ | $CH_3$ |
| I.1.70 | $CH(CH_3)CH_2OC_2H_5$ | $C_2H_5$ |
| I.1.71 | $CH(CH_3)CH_2OC_2H_5$ | $CH(CH_3)CH_2OC_2H_5$ |
| I.1.72 | $CH_2CH(CH_3)OC_2H_5$ | $CH_3$ |
| I.1.73 | $CH_2CH(CH_3)OC_2H_5$ | $C_2H_5$ |
| I.1.74 | $CH_2CH(CH_3)OC_2H_5$ | $CH_2CH(CH_3)OC_2H_5$ |

Extraordinary preference is also given to the compounds of formula I.2, in particular to the compounds of formulae I.2.1 to I.2.74 which differ from the corresponding compounds of formulae I.1.1 to I.1.74 in that $R^1$ is $C_2H_5$.

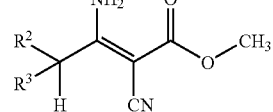

I.2

Extraordinary preference is also given to the compounds of formula I.3, in particular to the compounds of formulae I.3.1 to I.3.74 which differ from the corresponding compounds of formulae I.1.1 to I.1.74 in that $R^1$ is $nC_3H_7$.

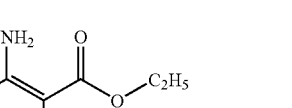

I.3

Extraordinary preference is also given to the compounds of formula I.4, in particular to the compounds of formulae I.4.1 to I.4.74 which differ from the corresponding compounds of formulae I.1 to I.1.74 in that $R^1$ is $nC_4H_9$.

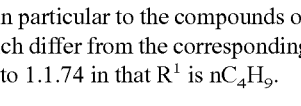

I.4

Extraordinary preference is also given to the compounds of formula I.5, in particular to the compounds of formulae I.5.1 to I.5.75 which differ from the corresponding compounds of formulae I.1.1 to I.1.75 in that $R^1$ is $CH_2CH=CH_2$.

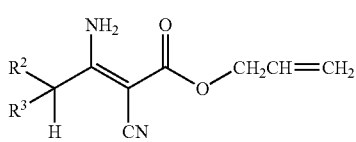

I.5

Extraordinary preference is also given to the compounds of formula I.6, in particular to the compounds of formulae I.6.1 to I.6.75 which differ from the corresponding compounds of formulae I.1.1 to I.1.75 in that $R^1$ is $CH_2CH=CHCH_3$.

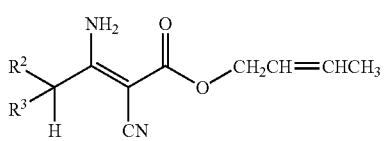

I.6

Extraordinary preference is also given to the compounds of formula I.7, in particular to the compounds of formulae I.7.1 to I.7.75 which differ from the corresponding compounds of formulae I.1.1 to I.1.75 in that $R^1$ is $(CH_2)_2CH=CH_2$.

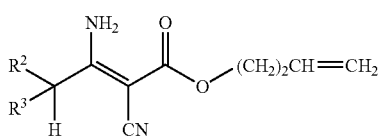

I.7

Extraordinary preference is also given to the compounds of formula I.8, in particular to the compounds of formulae I.8.1 to I.8.74 which differ from the corresponding compounds of formulae I.1.1 to I.1.74 in that $R^1$ is $(CH_2)_2OCH_3$.

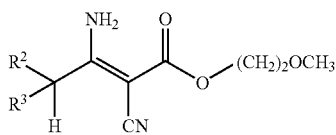

I.8

Extraordinary preference is also given to the compounds of formula I.9, in particular to the compounds of formulae I.9.1 to I.9.74 which differ from the corresponding compounds of formulae I.1.1 to 1.1.74 in that $R^1$ is $(CH_2)_2OCH_3$.

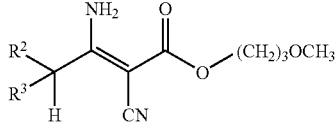

I.9

Extraordinary preference is also given to the compounds of formula I.10, in particular to the compounds of formulae I.10.1 to I.10.74 which differ from the corresponding compounds of the formulae I.1.1 to I.1.74 in that $R^1$ is $CH(CH_3)CH_2OCH_3$.

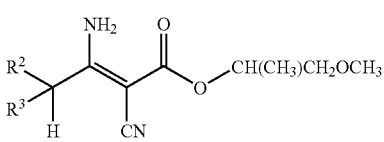

I.10

Extraordinary preference is also given to the compounds of formula I.11, in particular to the compounds of formulae I.11.1 to I.11.74 which differ from corresponding compounds of the formulae I.1.1 to I.1.74 in that $R^1$ is $CH_2CH(CH_3)_2OCH_3$.

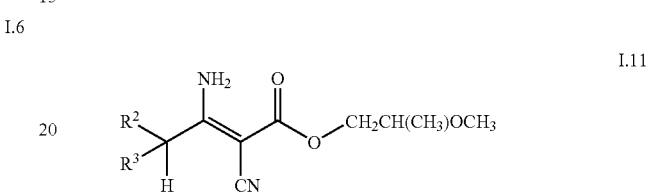

I.11

Extraordinary preference is also given to the compounds of formula I.12, in particular to the compounds of formulae I.12.1 to I.12.74 which differ from the corresponding compounds of formulae I.1.1 to I.1.74 in that $R^1$ is $(CH_2)_2OC_2H_5$.

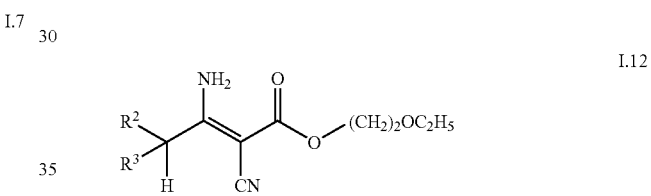

I.12

Extraordinary preference is also given to the compounds of formula I.13, in particular to the compounds of formulae I.13.1 to I.13.74 which differ from the corresponding compounds of formulae I.1.1 to I.1.74 in that $R^1$ is $(CH_2)_3OC_2H_5$.

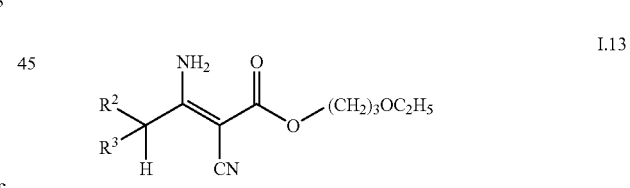

I.13

Extraordinary preference is also given to the compounds of formula I.14, in particular to the compounds of formulae I.14.1 to I.14.74 which differ from the corresponding compounds of formulae I.1.1 to I.1.74 in that $R^1$ is $CH(CH_3)CH_2OC_2H_5$.

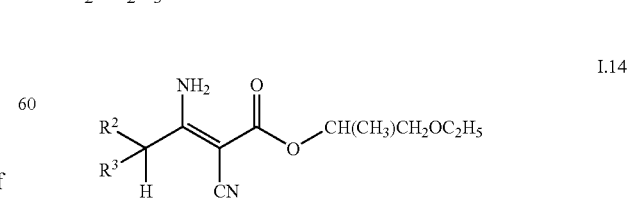

I.14

Extraordinary preference is also given to the compounds of formula I.15, in particular to the compounds of formulae I.15.1 to I.15.74 which differ from the corresponding compounds of formulae I.1.1 to I.1.74 in that $R^1$ is $CH_2CH(CH_3)OC_2H_5$.

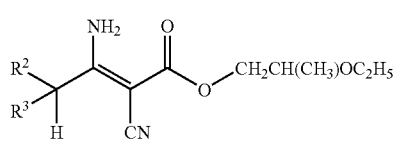

I.15

In the synthesis of the β-amino-α-cyanoacrylates, the starting materials or products in question are usually present in an (E):(Z) ratio of from 95:5 to 5:95. It is possible to separate the isomers, for example by chromatographic purification, and to continue the reactions with the pure isomer in question.

The β-amino-α-cyanoacrylates of formula I can be prepared by various routes, for example by the following processes:

Process A

Cyanoacetic esters of formula IV are reacted with carbonyl chlorides of formula V to give enoles of formula III. Following conversion of the enol OH-group, the corresponding enol ether of formula II is obtained, which is then converted with ammonia into the desired β-amino-α-cyanoacrylate:

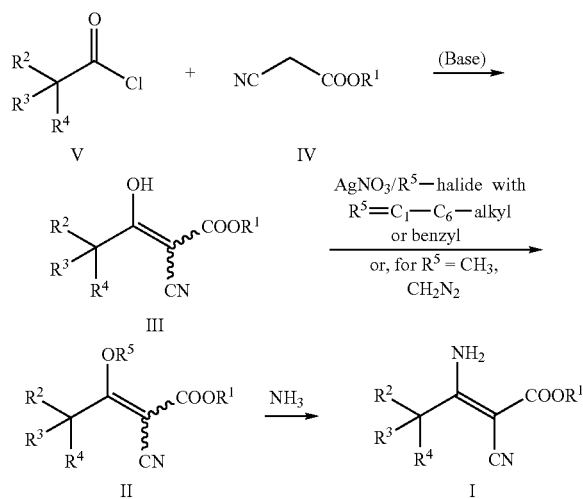

where $R^5$ is, for example, methyl, ethyl or benzyl

The conversion of the cyanoacetic ester of formula IV with carbonyl chlorides of the formula V into enoles of formula III is usually carried out at temperatures of from 0° C. to 15° C., preferably at 0° C., in an inert organic solvent, if appropriate in the presence of a base [cf. Haller et al., C. R. Acad. Sc. 15 (1887), 115; Dieckmann et al., Chem. Ber. 37 (1904), 3384; Michael et al., Chem. Ber. 38 (1905), 50; Guinchant, Ann. Chim. 9 (1918), 49].

Suitable solvents are aliphatic hydrocarbons such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, particularly preferably methylene chloride, tert-butyl methyl ether, diethyl ether, tetrahydrofuran and acetonitrile.

It is also possible to use mixtures of solvents mentioned.

Suitable bases are, in general, inorganic compounds, such as alkali metal and alkaline earth metal alkoxides, such as sodium methoxide, sodium ethoxide, potassium ethoxide, potassium tert-butoxide, potassium tert-pentoxide and dimethoxymagnesium, and furthermore organic bases, for example tertiary amines, such as trimethylamine, triethylamine, diisoproylethylamine and N-methylpiperidine, pyridine, substituted pyridines such as collidine, lutidine, N-methylmorpholine and 4-dimethylaminopyridine, and also bicyclic amines. Particular preference is given to sodium ethoxide and triethylamine.

The bases are generally employed in excess or they can, if appropriate, be used as solvent.

IV is generally employed in excess, based on V.

The reaction mixtures are worked up in a customary manner, for example by mixing with water, separation of the phases and, if appropriate, chromatographic purification of the crude products. Some of the intermediates and end products are obtained in the form of viscous oils which can be purified or freed from volatile components under reduced pressure and at moderately elevated temperature. If the intermediates and end products are obtained as solid, purification can also be carried out by recrystallization or digestion.

The enol ethers of formula II can be obtained by alkylation of the silver salt of the enol of formula III.

The reaction of the enol of formula III with silver nitrate is usually carried out in water at 25° C. [cf. Haller, Comp. Rend. 130 (1900), 1221].

The reaction of the silver salt of the enol ether of the formula III with an alkylating agent is usually carried out at from 25° C. to 80° C. in an inert organic solvent [cf. Haller, Comp. Rend. 130 (1900), 1221].

Suitable solvents are halogenated hydrocarbons, such as methylene chloride, chloroform and chlorobenzene, ethers, such as diethyl ether, diisopropyl ether, tert-butyl methyl ether, dioxane, anisole and tetrahydrofuran, and nitriles, such as acetonitrile and propionitrile, particularly preferably acetonitrile.

It is also possible to use mixtures of the solvents mentioned.

Suitable alkylating agents $R^5$-halides are alkyl halides with $R^5$=$C_1$-$C_6$-alkyl, such as, for example, methyl or ethyl iodide and also methyl or ethyl bromide. For converting III into II, it is furthermore also possible to use benzyl halides with $R^5$=benzyl, such as, for example, benzyl chloride or benzyl bromide.

In general, the alkylating agent is employed in an excess, based on the silver salt of the acrylocyanoacetic ester of formula III.

Work-up can be carried out in a manner known per se to afford the product.

For obtaining the enol ether of formula II wherein $R^5$ is methyl, the enol of formula III can also be reacted with diazomethane. This reaction is usually carried out at from 0° C. to 20° C. in an inert organic solvent [cf. Arndt et al., Liebigs Ann. 521 (1936), 108].

Suitable solvents are ethers, such as diethyl ether, diisopropyl ether, tert-butyl methyl ether, dioxane, anisole and tetrahydrofuran, particularly preferably diethyl ether.

It is also possible to use mixtures of the solvents mentioned.

The starting materials are generally reacted with each other in equimolar amounts. It may be advantageous to employ an excess of diazomethane, based on the enol of formula III.

Instead of diazomethane, it is also possible to use, for example, trimethylsilyldiazomethane.

Work-up can be carried out in a manner known per se to afford the product.

The enol ethers of formula II can also be obtained by reacting, for example, orthoesters of formula VII, where $R^5$ is a $C_1$-$C_4$-alkyl radical, such as, for example, methyl or ethyl, with the appropriate cyanoacetic esters of formula IV:

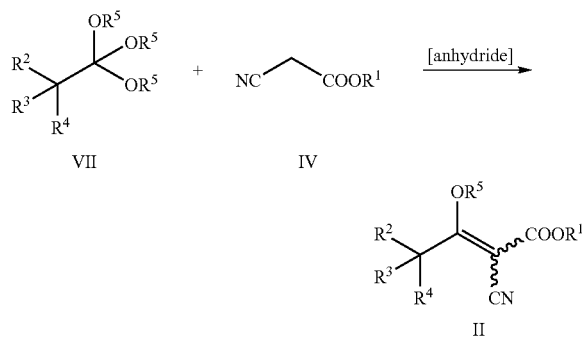

where $R^5 = C_1$-$C_4$-alkyl

This reaction is usually carried out at from 100° C. to 150° C., preferably at from 110° C. to 130° C., in the presence of a carboxylic anhydride [cf. Xia et al., J. Med. Chem. 40 (1997), 4372].

Suitable solvents are carboxylic anhydrides, such as acetic anydride or propionic anhydride.

In general, an excess of VII is employed, based on IV.

The orthoesters required for preparing the compounds VI are known from the literature [cf. Houben-Weyl, 1965, Vol. 6/3, 300 f.], or they can be prepared in accordance with the literature cited and/or are commercially available.

The reaction of the enol ethers of the formula II with ammonia or an ammonia-containing solution is usually carried out at from 0° C. to 20° C., preferably from 0° C. to 10° C., in an inert organic solvent [cf. Haller, Comp. Rend. 130 (1900), 1221].

Suitable solvents are ethers, such as diethyl ether, diisopropyl ether, tert-butyl methyl ether, dioxane, anisole and tetrahydrofuran, nitrites, such as acetonitrile and propionitrile, alkohols, such as methanol, ethanol, n-propanol, isopropanol, n-butanol and tert-butanol, particularly preferably acetonitrile.

It is also possible to use mixtures of the solvents mentioned.

In general, an excess of ammonia is employed, based on II.

Work-up can be carried out in a manner known per se to afford the product.

The starting materials required for preparing the compounds I are known from the literature [Dahn et al., Helv. Chim. Acta 42 (1959), 1214; Bowie, Tetrahedron 23 (1967), 305], or they can be prepared in accordance with the literature cited and/or are commercially available.

Process B

Enoles of formula III are reacted with acid chlorides $R^6COCl$ to give enol esters of formula VI, which are then reacted with ammonia to give the desired β-amino-α-cyanoacrylates:

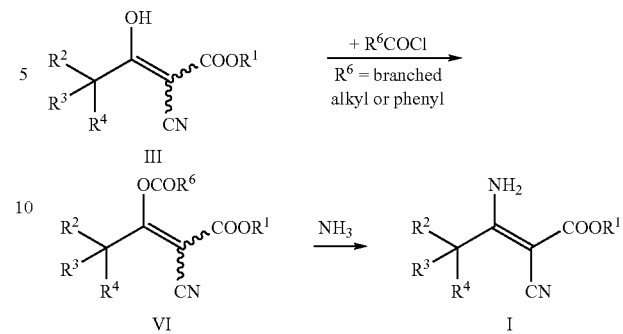

$R^6COCl$ are customary acid chlorides which are commercially available, such as, for example, acetic acid chloride, isobutyryl chloride or pivaloyl chloride. $R^6$ is $C_1$-$C_6$-alkyl (such as, for example, methyl, ethyl, isopropyl or tert.-butyl), phenyl or benzyl. Preference is given to acid chlorides having sterically demanding radicals $R^6$, such as, for example, branched $C_3$-$C_6$-alkyl or phenyl.

The conversion of the enoles of formula III with acid chlorides into enol esters of formula VI is usually carried out at from 0° C. to 35° C., preferably at 25° C., in an inert organic solvent in the presence of a base [cf. Haller, Comp. Rend. 130 (1900), 1221; Schmitt, Bull. Soc. Chim. France 31 (1904), 325].

Suitable solvents are aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, particularly preferably acetonitrile.

It is also possible to use mixtures of the solvents mentioned.

Optionally the reaction can be carried out in the presence of a base.

Suitable bases are, in general, inorganic compounds, such as alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal and alkaline earth metal alkoxides, such as sodium methoxide, sodium ethoxide, potassium ethoxide, potassium tert-butoxide, potassium tert-pentoxide and dimethoxymagnesium, furthermore organic bases, for example tertiary amines, such as trimethylamine, triethylamine, diisopropylethylamine, N-methylpiperidine, pyridine, substituted pyridines, such as collidine, lutidine and 4-dimethylaminopyridine, and also bicyclic amines. Particular preference is given to alkoxides.

The bases are generally employed in equimolar amounts.

The starting materials are generally reacted with one another in equimolar amounts. It may be advantageous to employ an excess of acid chloride, based on III.

Work-up can be carried out in a manner known per se to afford the product.

The enoles of the formula III required for preparing the compounds VI can be prepared according to Process A.

The reaction of the enol esters of the formula VI with ammonia or an ammonia-containing solution is carried out under the same conditions as described in Process A.

Process C

Reaction of the enoles of formula III with POCl$_3$ and subsequent reaction of the crude reaction mixture with ammonia likewise gives β-amino-α-cyanoacrylates of formula I:

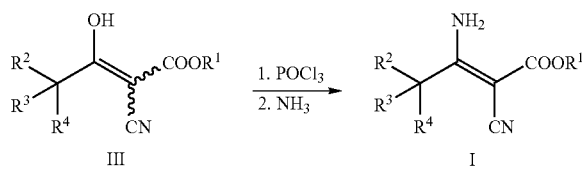

The reaction with POCl$_3$ is usually carried out at from 0° C. to 100° C., preferably at 0 to 50° C., particular preferably 0 to 25° C., most preferably at 0° C., in an inert organic solvent in the presence of a base [cf. DE 1 935 630].

Suitable solvents for the reaction with POCl$_3$ are aromatic hydrocarbons, such as toluene, o-, m- and p-xylene, halogenated hydrocarbons, such as methylene chloride, chloroform and chlorobenzene, particularly preferably methylene chloride, chloroform and toluene.

It is also possible to use mixtures of the solvents mentioned.

Suitable bases are, in general, organic bases, for example tertiary amines, such as trimethylamine, triethylamine, diisopropylethylamine, N-methylpiperidine, pyridine, substituted pyridines, such as collidine, lutidine and 4-dimethylaminopyridine, and also bicyclic amines. Particular preference is given to triethylamine.

The bases are generally employed in excess.

Following gentle concentration of the reaction mixture, the subsequent reaction with ammonia, of the enol phosphate formed in the reaction is preferably carried out in nitriles, such as acetonitrile or propionitrile.

In general, an excess of POCl$_3$ and NH$_3$ is used, based on III.

Process D

The reaction of imido esters of formula VIII, previously released, for example, from the corresponding hydrochlorides using a base, with cyanoacetic esters of formula IV also gives β-amino-α-cyanoacrylates of formula I:

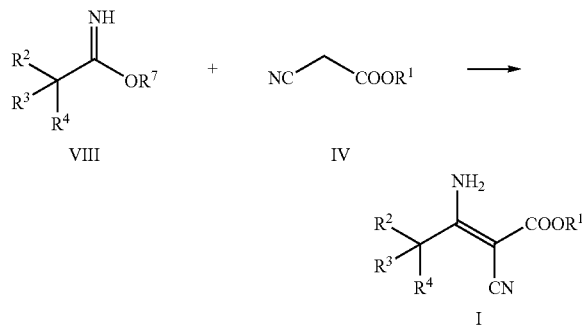

where R$^7$=C$_1$-C$_6$-alkyl

R$^7$ is a C$_1$-C$_6$-alkyl radical such as, for example, methyl or ethyl.

The imido esters are usually released from their salts using bases, such as potassium carbonate [cf. Houben-Weyl 1952, Vol. 8, 697].

The reaction with cyanoacrylates of formula IV is usually carried out at from 50° C. to 100° C., preferably at from 80° C. to 90° C., in an organic solvent [cf. Kenner et al., J. Chem. Soc. 1943, 388].

Suitable solvents are ethers, such as dioxane, anisole and tetrahydrofuran, nitrites, such as acetonitrile and propionitrile, alcohols, such as methanol, ethanol, n-propanol, isopropanol, n-butanol and tert-butanol, particularly preferably ethanol.

It is also possible to use mixtures of other solvents mentioned.

The starting materials are generally reacted with one another in equimolar amounts. It may be advantageous to employ an excess of VIII, based on IV.

The imido ester hydrochlorides required for preparing the compounds I are known from the literature [cf. Pinner, Die Iminoäther und ihre Derivate, [The imino ethers and their derivatives], Berlin 1892] or they can be prepared in accordance with the literature cited especially from the respective nitrites.

Process E

The reaction of amidines of formula IX, previously released, for example, from the corresponding hydrochlorides using a base, with cyanoacetic esters of formula IV also gives β-amino-α-cyanoacrylates of the formula I:

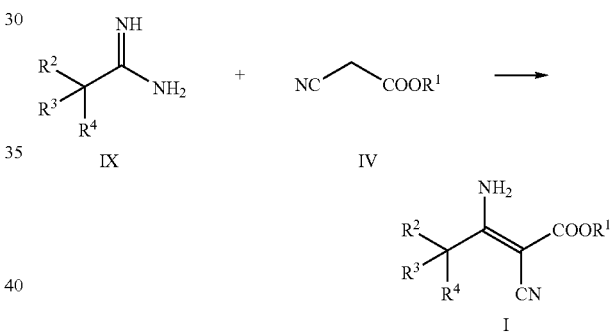

The amidines are usually released from their salts using bases, such as, for example, potassium carbonate (cf. Houben-Weyl 1952, Vol. 8, 702).

The reaction with cyanoacrylates of formula IV is usually carried out at from 80° C. to 130° C., preferably at from 90° C. to 100° C., in an inert organic solvent [cf. Hull et al., J. Chem. Soc. 1946, 357]

Suitable solvents are aromatic hydrocarbons, such as toluene, o-, m- and p-xylene, alcohols, such as ethanol, n-propanol, isopropanol, n-butanol and tert-butanol, particularly preferably ethanol.

Suitable bases for releasing the amidines from their salts are, in general, inorganic compounds, such as alkali metal and alkaline earth metal carbonates, such as lithium carbonate, potassium carbonate and calcium carbonate, and also alkali metal and alkaline earth metal alkoxides, such as sodium methoxide, sodium ethoxide, potassium ethoxide, potassium tert-butoxide, potassium tert-pentoxide, and furthermore ammonia. Particular preference is given to potassium carbonate and ammonia.

The starting materials are generally reacted with one another in equimolar amounts. It may be advantageous to employ an excess of IX, based on IV.

The amidine hydrochlorides required for preparing the compounds I are known from the literature [Houben-Weyl; 1952, Vol. 8, 702 f.], or they can be prepared in accordance with the literature cited.

The present invention also provides novel enol ethers of formula II

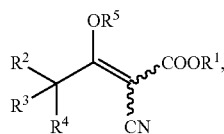

where $R^1$ to $R^4$ have the meanings mentioned for the compounds of formula I and $R^5$ is $C_1$-$C_6$-alkyl (such as, for example, methyl or ethyl) or benzyl.

The enol ethers of the formula II are present as an (E)/(Z) mixture in a ratio of from 95:5 to 5:95. It is possible to separate the isomers, for example by chromatographic methods.

With respect to the variables, the particularly preferred embodiments of the intermediates correspond to those of radicals $R^1$ to $R^4$ of formula I.

Particular preference is given to the compounds of the formula II in which $R^1$ is n $C_1$-$C_4$-alkyl;

particularly preferably methyl, ethyl or n-propyl;

$R^2,R^3$ are $C_1$-$C_4$-alkyl;

particularly preferably methyl or ethyl; and $R^4$ is hydrogen, fluorine or chlorine;

particularly preferably hydrogen.

The present invention alsoprovides novel enol esters of formula VI

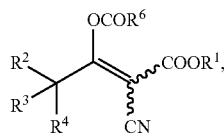

where $R^1$ to $R^4$ have the meanings mentioned for the compounds of formula I and $R^6$ is $C_1$-$C_6$-alkyl (such as, for example, isopropyl, tert-butyl, preferably tert-butyl), phenyl or benyl.

The enol esters of formula VI are present as an (E)/(Z) mixture in a ratio of from 95:5 to 5:95, usually in a ratio of 50:50. It is possible to separate the isomers, for example by chromatographic methods.

With respect to the variables, the particularly preferred embodiments of the intermediates correspond to those of radicals $R^1$ to $R^4$ in the formula I.

Particular preference is given to the compounds of formula VI in which $R^1$ is n-$C_1$-$C_4$-alkyl;

particularly preferably methyl, ethyl or n-propyl;

$R^2,R^3$ are $C_1$-$C_4$-alkyl;

particularly preferably methyl or ethyl; and $R^4$ is hydrogen, fluorine or chlorine;

particularly preferably hydrogen.

EXAMPLE 2.1

Ethyl (2Z)-3-amino-2-cyano-4-ethyl-2-hexenoate

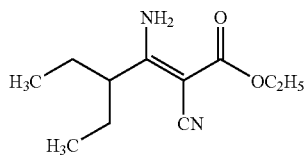

EXAMPLE 2.1

1.a Ethyl 2-cyano-3-hydroxy-4-ethyl-2-hexenoate

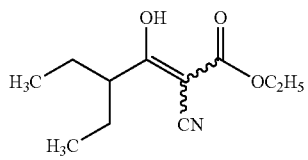

At 0° C., 74 g (0.55 mol) of 2-ethylbutyryl chloride were added dropwise to a suspension of 150 g (1.1 mol) of sodium cyanoacetate ethyl ester in diethyl ether. The reaction mixture was stirred at 25° C. for 16 h and then hydrolyzed, and the organic phase was separated off. The aqueous phase was washed with ether and then acidified to pH 3. The enol released in this manner was extracted, washed and dried. Customary purification gave 81 g (70% of theory) of the title compound as a viscous colorless liquid (b.p. 78 to 81° C./1.2 mbar).

1.b Ethyl 2-cyano-3-hydroxy-4-ethyl-2-hexenoate

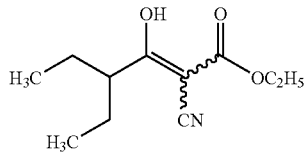

With ice-cooling, 227 g (2.15 mol) of triethylamine were poured into a solution of 170 g (1.5 mol) of ethyl cyanoacetate in acetonitrile, and 101 g (0.75 mol) of 2-ethylbutyryl chloride were added dropwise at from 10 to 25° C. After 2 h of stirring at 25° C., the mixture was concentrated and the residue was dissolved in MTBE (methyl tert-butyl ether). By washing with 5% strength NaOH, the enolate was transferred into the aqueous phase, from which it was released by acidification to pH 3. The acidic aqueous solution was extracted and the extract was dried and concentrated. Customary purification gave 100 g (63% of theory) of the title compound as an oil (b.p. 78 to 80° C./1.5 mbar).

2.a Ethyl 2-cyano-3-methoxy-4-ethyl-2-hexenoate Using AgNO₃/methyl Iodide

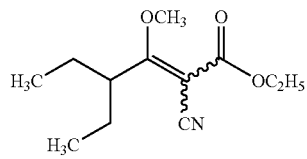

181 g (0.8 mol) of ethyl 2-cyano-3-hydroxy-4-ethyl-2-hexenoate were dissolved in water, and an aqueous solution of 150 g of silver nitrate was added. The precipitate was filtered off with suction, washed and dried. This gave 188 g (74% of theory) of the silver salt of ethyl 2-cyano-3-hydroxy-4-ethyl-2-hexenoate.

At 25° C., 142 g (1 mol) of methyl iodide were added dropwise to a suspension of 188 g (0.59 mol) of the silver salt of ethyl 2-cyano-3-hydroxy-4-ethyl-2-hexenoate in acetonitrile, and the mixture was then heated at the boil for 3 h. The precipitated AgI was filtered off with suction, and the filtrate was then concentrated and dissolved in $CH_2Cl_2$. The organic phase was washed, dried and concentrated. Customary purification gave 52 g (39% of theory) of the title compound.

2.b Ethyl 2-cyano-3-[(pivaloyl)oxy]-4-ethyl-2-hexenoate

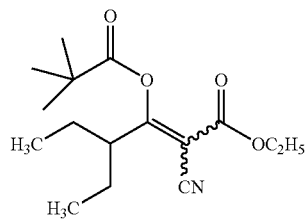

36 g (0.17 mol) of ethyl 2-cyano-3-hydroxy-4-ethyl-2-hexenoate were dissolved in ethanol, and 31 g (0.17 mol) of 30% strength $NaOCH_3$ solution were added. The mixture was then concentrated to dryness, and the sodium enolate was released by adding toluene and reconcentration of alcohol residues. 39.7 g (0.17 mol) of the resulting sodium salt were initially charged in acetonitrile and, at 0° C. with warming to 20° C., mixed dropwise with 27.4 g (0.23 mol) of pivaloyl chloride. After 16 g of stirring at 25° C., the reaction mixture was concentrated and the residue was taken up in ethyl acetate and washed with 2% strength NaOH. The organic phase was dried and concentrated. Customary purification gave 41.5 g (83% of theory) of the title compound (b.p. 102° C./1 mbar).

3.a Ethyl (2Z)-3-amino-2-cyano-4-ethyl-2-hexenoate

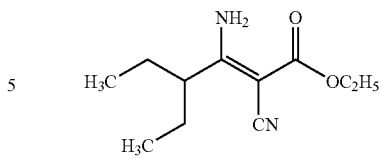

At 10° C., 52 g (0.23 mol) of ethyl 2-cyano-3-methoxy-4-ethyl-2-hexenoate were initially charged in THF, and 20 g (0.3 mol) of 25% strength ammonia solution were added. After 2 h of stirring at 25° C., the solution was concentrated, the residue was taken up in n-hexane/diisopropyl ether (1:1) and the precipitate was filtered off with suction.

The mother liquor was purified using customary purification methods. This gave 11.7 g of a product mixture from which, by recrystallization with diisopropyl ether, 4 g (8% of theory) of the title compound (m.p. 85° C.) were isolated.

3.b Ethyl (2Z)-3-amino-2-cyano-4-ethyl-2-hexenoate

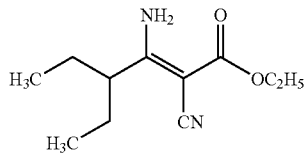

118.2 g (0.4 mol) of ethyl 2-cyano-3-[(pivaloyl)oxy]-4-ethyl-2-hexenoate were dissolved in acetonitrile and cooled to 10° C. At 10-15° C., 112 g (0.8 mol) of 25% strength ammonia solution were then added dropwise, and the mixture was stirred at 15° C. for 3 h. The organic phases is [sic] washed, dried and concentrated. Recrystallization with diisopropyl ether gave 57.5 g (68% of theory) of the title compound (m.p. 87° C.).

EXAMPLE 2.2 n-Propyl (2Z)-3-amino-2-cyano-4-ethyl-2-hexenoate

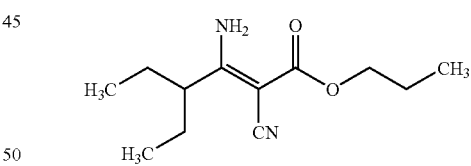

EXAMPLE 2.2

Analogously to the preparation of ethyl 2-cyano-3-hydroxy-4-ethyl 2-hexenoate, n-propyl 2-cyano-3-hydroxy-4-ethyl-2-hexenoate was prepared from n-propyl cyanoacetate and 2-ethylbutyryl chloride.

25.5 g (0.11 mol) of n-propyl 2-cyano-3-hydroxy-4-ethyl-2-hexenoate were then dissolved in $CH_2Cl_2$, and 35 g (0.23 mol) of $POCl_3$ were added. At 0° C., 48 g (0.47 mol) of triethylamine were then added dropwise, and the mixture was stirred at 25° C. for 3 h. The reaction solution was concentrated and the residue was dissolved in acetonitrile. At 0° C., 50 ml (0.65 mol) of 25% strength ammonia solution were then added dropwise to this solution, and the mixture was stirred overnight.

The solution was then washed, dried and concentrated. Customary purification gave 12.8 g (52% of theory) of the title compound as a white solid (m.p. 84° C.).

EXAMPLE 2.3 n-Propyl (2Z)-3-amino-2-cyano-4-[(methylsulfanyl)methyl]-2-hexenoate

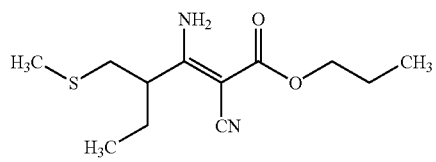

EXAMPLE 2.3

1. n-Propyl 2-cyano-3-hydroxy-4-[(methylsulfanyl)methyl]-2-hexenoate

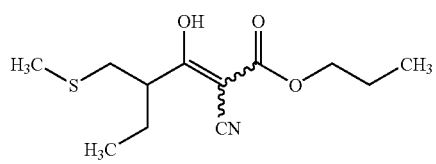

At 25° C., 16.7 g (0.1 mol) of 2-[(methylsulfanyl)methyl]butyryl chloride were added to a solution of 12.7 g (0.1 mol) of n-propyl cyanoacetate in $CH_2Cl_2$, and the mixture was cooled to 0° C. At 0° C., 20.2 g (0.2 mol) of triethylamine were then added dropwise. After 16 h of stirring at 25° C., the reaction mixture was hydrolyzed and the organic phase was separated off, dried and concentrated. Customary purification gave 15 g (58% of theory) of the title compound as a yellow liquid (b.p. 118 to 120° C./2 mbar).

2. n-Propyl (2Z)-3-amino-2-cyano-4-[(methylsulfanyl)methyl]-2-hexenoate

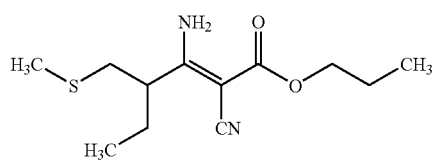

15 g (58.3 mmol) of n-propyl-2-cyano-3-hydroxy-4-[(methyl-sulfanyl)methyl]-2-hexenoate were dissolved in $CH_2Cl_2$, and 18 g (0.12 mmol) of $POCl_3$ were added. At 0° C., 24 g (237 mmol) of triethylamine were then added dropwise, and the mixture was stirred at 25° C. for 2 h. The reaction solution was concentrated and the residue was dissolved in acetonitrile. At 0° C., 50 ml (650 mmol) of 25% strength ammonia solution were then added dropwise to this solution, and the mixture was stirred for 1 h.

The solution was then washed, dried and concentrated. Customary purification gave 5.8 g (52% of theory) of the title compound as a brownish solid (m.p. 78° C.).

The compounds listed in Table 2 below can be prepared analogously to the above processes:

TABLE 2

| No. | $R^1$ | $R^2$ | $R^3$ | $R^4$ | m.p. [° C.] |
|---|---|---|---|---|---|
| 2.1 | $C_2H_5$ | $C_2H_5$ | $C_2H_5$ | H | 85-87 |
| 2.2 | $nC_3H_7$ | $C_2H_5$ | $C_2H_5$ | H | 84 |
| 2.3 | $C_2H_5$ | $CH_2SCH_3$ | $C_2H_5$ | H | 78 |
| 2.4 | $CH_3$ | $CH_3$ | $C_2H_5$ | H | |
| 2.5 | $CH_3$ | $C_2H_5$ | $C_2H_5$ | H | 65 |
| 2.6 | $C_2H_5$ | $CH_3$ | $C_2H_5$ | H | 102-103 |
| 2.7 | $C_2H_5$ | $C_2H_5$ | $nC_4H_9$ | H | 83 |
| 2.8 | $C_2H_5$ | $CH_3$ | $CH_3$ | $C_2H_5$ | 65-67 |
| 2.9 | $C_2H_5$ | $CH_3$ | $CH_3$ | Cl | 56 |
| 2.10 | $C_2H_5$ | $CH_3$ | $CH_3$ | Br | 46 |
| 2.11 | $nC_3H_7$ | $C_2H_5$ | $C_2H_5$ | H | |
| 2.12 | $C_2H_5$ | cyclopropyl | | | |
| 2.13 | $C_2H_5$ | 2,2-dichloro-3-ethyl-cyclopropyl | | H | |
| 2.14 | $C_2H_5$ | cyclopentyl | | H | 110-112 |
| 2.15 | $C_2H_5$ | cyclohexyl | | H | 105-106 |
| 2.16 | $C_2H_5$ | tetrahydrofuryan-3-yl | | H | Oil |
| 2.17 | $C_2H_5$ | tetrahydropyran-4-yl | | H | 148-150 |
| 2.18 | $C_2H_5$ | tetrahydropyran-3-yl | | H | Oil |
| 2.19 | $nC_3H_7$ | tetrahydropyran-3-yl | | H | 150-152 |
| 2.20 | $C_2H_5$ | tetrahydrothiopyran-3-yl | | H | 124 |
| 2.21 | $CH_2CHCH_2$ | $C_2H_5$ | $C_2H_5$ | H | 72 |
| 2.22 | 2-Methoxyethyl | $C_2H_5$ | $C_2H_5$ | H | 70 |
| 2.23 | 2-Ethoxyethyl | $C_2H_5$ | $C_2H_5$ | H | 70 |
| 2.24 | $CH(CH_3)CH_2OCH_3$ | $C_2H_5$ | $C_2H_5$ | H | 150 |
| 2.25 | $C_2H_5$ | $nC_3H_7$ | $nC_3H_7$ | H | 110-112 |
| 2.26 | $CH_2CH=CHCH_3$ | $C_2H_5$ | $C_2H_5$ | H | 100 |
| 2.27 | $C_2H_5$ | $C_2H_5$ | $nC_3H_7$ | H | |
| 2.28 | $C_2H_5$ | $CH=CHCH_3$ | $C_2H_5$ | H | 82 |
| 2.29 | $nC_3H_7$ | $CH_2OCH_3$ | $C_2H_5$ | H | Öl |
| 2.30 | $C_4H_9$ | $C_2H_5$ | $C_2H_5$ | H | 80 |

Biological Application

The β-amino-α-cyanoacrylates of the formula I and their agriculturally useful salts are suitable for use as herbicides. The herbicidal compositions comprising compounds of the formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method, the compounds in question of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum,*

*Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays*.

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should ensure the finest possible distribution of the active compounds according to the invention.

The herbicidal compositions comprise a herbicidally effective amount of at least one compound of the formula I or an agriculturally useful salt of I and auxiliaries customary for formulating crop protection agents.

Suitable inert auxiliaries are essentially:

mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, ligninsulfite waste liquors or methylcellulose.

Powders, materials for spreading and dusts can be prepared by mixing or grinding the active compounds together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound. The active compounds are employed in a purity of from 90% to 100%, preferably 95% to 100% (according to NMR spectrum).

The formulation examples which follow illustrate the preparation of such products:

I. 20 parts by weight of compound of the formula I are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound of the formula I.

II. 20 parts by weight of compound of the formula I are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound of the formula I.

III. 20 parts by weight of compound of the formula I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound of the formula I.

IV. 20 parts by weight of compound of the formula I are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound of the formula I.

V. 3 parts by weight of compound of the formula I are mixed with 97 parts by weight of finely divided kaolin. This gives a dust which comprises 3% by weight of active compound of the formula I.

VI. 20 parts by weight of compound of the formula I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of compound of the formula I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of compound of the formula I is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The active compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The rates of application of active compound of the formula I are from 0.001 to 3.0, preferably 0.01 to 1.0, kg/ha of active substance (a.s.), depending on the control target, the season, the target plants and the growth stage.

To widen the spectrum of action and to achieve synergistic effects, the β-amino-α-cyanoacrylates of the formula I may be mixed with a large number of representatives of other herbicidal or growth-regulating active compounds and then applied concomitantly. Suitable components for mixtures are, for example, 1,2,4-thiadiazoles, 1,3,4-thiadiazoles, amides, aminophosphoric acid and its derivatives, aminotriazoles, anilides, aryl/hetaryl-oxyalkanoic acids and their derivatives, benzoic acid and its derivatives, benzothiadiazinones, 2-(hetaroyl/aroyl)-1,3-cyclohexanediones, hetaryl aryl ketones, benzyl-isoxazolidinones, meta-$CF_3$-phenyl derivatives, carbamates, quinolinecarboxylic acid and its derivates, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

The herbicidal activity of the β-amino-α-cyanoacrylates of the formula I was demonstrated by the following greenhouse experiment:

The cultivation containers used were plastic flowerpots containing loamy sand with approximately 3.0% of humus as the substrate. The seeds of the test plants were sown separately for each species.

For the pre-emergence treatment, directly after sowing the active compounds, which had been suspended or emulsified in water, were applied by means of finely distributing nozzles. The containers were irrigated gently to promote germination and growth and subsequently covered with transparent plastic hoods until the plant had rooted. This cover caused uniform germination of the test plants, unless this was adversely affected by the active compounds. The application rate for a pre-emergence treatment was 0.5 or 1.0 kg of a.s. (active substance)/ha.

For the post-emergence treatment, the test plants were first grown to a height of from 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.5 or 1.0 kg of a.s. (active substance)/ha.

Depending on the species, the plants were kept at from 10 to 25° C. or from 20 to 35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth.

The plants used in the greenhouse experiments were of the following species:

| Scientific name | Common name |
| --- | --- |
| *Amaranthus retroflexus* | pig weed |
| *Digitaria sanguinalis* | hairy fingergrass |
| *Pharbitis purpurea* | common morningglory |
| *Setaria faberii* | giant foxtail |

The effect of example 2.1, applied by the pre-emergence method at application rates of 1.0 kg/ha, on the harmful plants *Amaranthus retroflexus* and *Setaria faberii* is very good.

At application rates of 1.0 kg/ha, example 2.1 showed very good post-emergence activity against the undesirable plants *Pharbitis purpurea* and *Setaria faberii*.

The effect of example 2.2 applied by the pre-emergence method at application rates of 1.0 kg on the harmful plants *Digitaria sanguinalis* and *Setaria faberii* was very good.

At an application rate of 1.0 kg/ha, examples 2.22 and 2.25 have shown very good pre-emergence activity against the undesirable plant *Setaria faberii*.

The effect of example 2.21 applied under the same conditions at application rates of 0.5 kg/ha on the harmful plants *Digitaria sanguinalis* and *Setaria faberii* was very good.

At an application rate of 1.0 kg/ha examples 2.2, 2.22 and 2.25 have shown very good past-emergence activity against the undesirable plants *Pharbitis purpurea*.

We claim:
1. A β-amino-α-cyanoacrylate of formula I

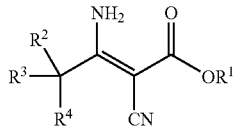

where the variables have the following meanings:
$R^1$ is n-$C_1$-$C_6$-alkyl, n-$C_3$-$C_6$-alkenyl or $C_1$-$C_6$-alkoxy-$C_1$-$C_4$-alkyl;
$R^2$, $R^3$ are $C_1$-$C_6$-alkyl, which may be partially or fully halogenated and/or may carry a substituent from the group consisting of cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl and $C_1$-$C_6$-haloalkylsulfonyl, are $C_2$-$C_6$-alkenyl or $C_2$-$C_6$-alkynyl;
$R^4$ is hydrogen, halogen, cyano or $C_1$-$C_6$-alkyl,
where, if $R^1$ is n-$C_1$-$C_6$-alkyl, the substituents $R^2$, $R^3$ and $R^4$ or two of the radicals $R^2$, $R^3$ and $R^4$ are not simultaneously methyl, or an agriculturally useful salt thereof.

2. A β-amino-α-cyanoacrylate of formula I as claimed in claim 1 in which $R^1$ is n-$C_1$-$C_6$-alkyl.

3. A β-amino-α-cyanoacrylate of formula I as claimed in claim 1 in which $R^1$ is n-$C_3$-$C_6$-alkenyl.

4. A β-amino-α-cyanoacrylate of formula I as claimed in claim 1 in which $R^2$ and $R^3$ are $C_1$-$C_6$-alkyl.

5. A β-amino-α-cyanoacrylate of formula I as claimed in claim 1 in which $R^4$ is hydrogen.

6. A β-amino-α-cyanoacrylate of formula I as claimed in claim 1 in which
$R^1$ is n-$C_1$-$C_6$-alkyl or n-$C_3$-$C_6$-alkenyl;
$R^2$, $R^3$ are $C_1$-$C_4$-alkyl; and
$R^4$ is hydrogen.

7. A process for preparing α-cyanoacrylates of formula I as claimed in claim 1, which comprises reacting an enol ether of formula II

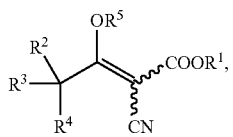

where $R^1$, $R^2$, $R^3$ and $R^4$ are as defined under claim 1 and $R^5$ is $C_1$-$C_6$-alkyl or benzyl, with ammonia;
where, if $R^1$ is n-$C_1$-$C_6$-alkyl, the substituents $R^2$, $R^3$ and $R^4$ or two of the radicals $R^2$, $R^3$ and $R^4$ are not simultaneously methyl.

8. A process for preparing α-cyanoacrylates of formula I as claimed in claim 1, which comprises reacting an enol ester of formula VI

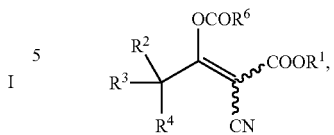

where $R^1$, $R^2$, $R^3$ and $R^4$ are as defined under claim 1 and $R^6$ is $C_1$-$C_6$-alkyl, phenyl or benzyl, with ammonia.

9. A process for preparing α-cyanoacrylates of formula I as claimed in claim 1, which comprises reacting an imido ester of formula VIII

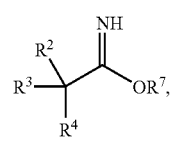

where $R^2$, $R^3$ and $R^4$ are as defined under claim 1 and $R^7$ is an $C_1$-$C_6$-alkyl radical,
with a cyanoacetic ester of formula IV

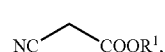

where $R^1$ is as defined in claim 1.

10. A process for preparing α-cyanoacrylates of formula I as claimed in claim 1, which comprises reacting an amidine of formula IX

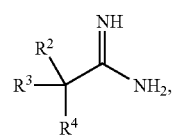

where $R^2$, $R^3$ and $R^4$ are as defined under claim 1 with a cyanoacetic ester of formula IV

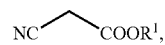

where $R^1$ is as defined in claim 1.

11. Enol ether of formula II

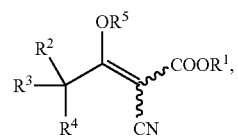

wherein $R^1$ is $C_3$-$C_6$-alkenyl, $R^2$ to $R^4$ are as defined under claim 1, and $R^5$ is $C_1$-$C_6$-alkyl or benzyl.

12. Enol esters of formula VI

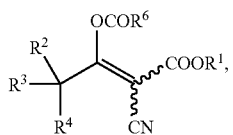

VI wherein $R^1$ to $R^4$ are as defined under claim 1 and $R^6$ is $C_1$-$C_6$-alkyl, phenyl or benzyl.

13. A composition, comprising a herbicidally effective amount of at least one α-cyanoacrylates of formula I or an agriculturally useful salt thereof as claimed in claim 1 and auxiliaries customary for formulating crop protection agents.

14. A process for preparing compositions as claimed in claim 13, which comprises mixing a herbicidally effective amount of at least one α-cyanoacrylates of formula I or an agriculturally useful salt thereof and auxiliaries customary for formulating crop protection agents.

15. Method for controlling undesirable vegetation, which comprises applying a herbicidally effective amount of at least one α-cyanoacrylates of formula I or an agriculturally useful salt thereof as claimed in claim 1 to plants, their habitat and/or seed.

* * * * *